United States Patent [19]

deMey et al.

[11] 4,311,387
[45] Jan. 19, 1982

[54] FLOW-THROUGH SAMPLE CELL AND COLLECTING AND ILLUMINATING OPTICS FOR LIQUID CHROMATOGRAPHY

[75] Inventors: Charles F. deMey, West Redding; Eugene F. Young, Wilton, both of Conn.

[73] Assignee: The Perkin-Elmer Corporation, Norwalk, Conn.

[21] Appl. No.: 103,788

[22] Filed: Dec. 14, 1979

[51] Int. Cl.³ .................... G01N 21/64; G01N 21/05
[52] U.S. Cl. ............................... 356/318; 250/461 R; 356/244; 356/410
[58] Field of Search ............... 356/244, 301, 317, 318, 356/410, 411; 250/458, 461 R, 461 B

[56] References Cited

U.S. PATENT DOCUMENTS

| | | | |
|---|---|---|---|
| 3,946,239 | 3/1976 | Salzman et al. | 250/461 B |
| 4,022,529 | 5/1977 | White | 356/318 |
| 4,088,407 | 5/1978 | Schoeffel et al. | 356/317 |
| 4,099,872 | 7/1978 | White | 356/318 |
| 4,176,956 | 12/1979 | Tomoff et al. | 356/244 |

OTHER PUBLICATIONS

Perkin-Elmer Brochure Entitled "Perkin-Elmer Model 3000 Fluorescence Spectrometer", No. K10-10-8-01894.
"Stroboscopic Time-Resolved Spectroscopy," Bhaumik et al., Rev. Sci. Inst., vol. 36 #1, Jan. 1965, pp. 37–40.
"An Efficient Light Collector," Brown, Rev. Sci. Inst., vol. 42, No. 5, May 1971, p. 729.

Primary Examiner—Vincent P. McGraw
Attorney, Agent, or Firm—S. A. Giarratana; F. L. Masselle; R. A. Hays

[57] ABSTRACT

The present invention includes an apparatus for measuring radiation from a sample. The apparatus includes means for axially focusing radiation from an excitation monochromator at the sample. The present invention further includes a novel sample cell holder useful with the fluorescent radiation measuring apparatus.

15 Claims, 5 Drawing Figures

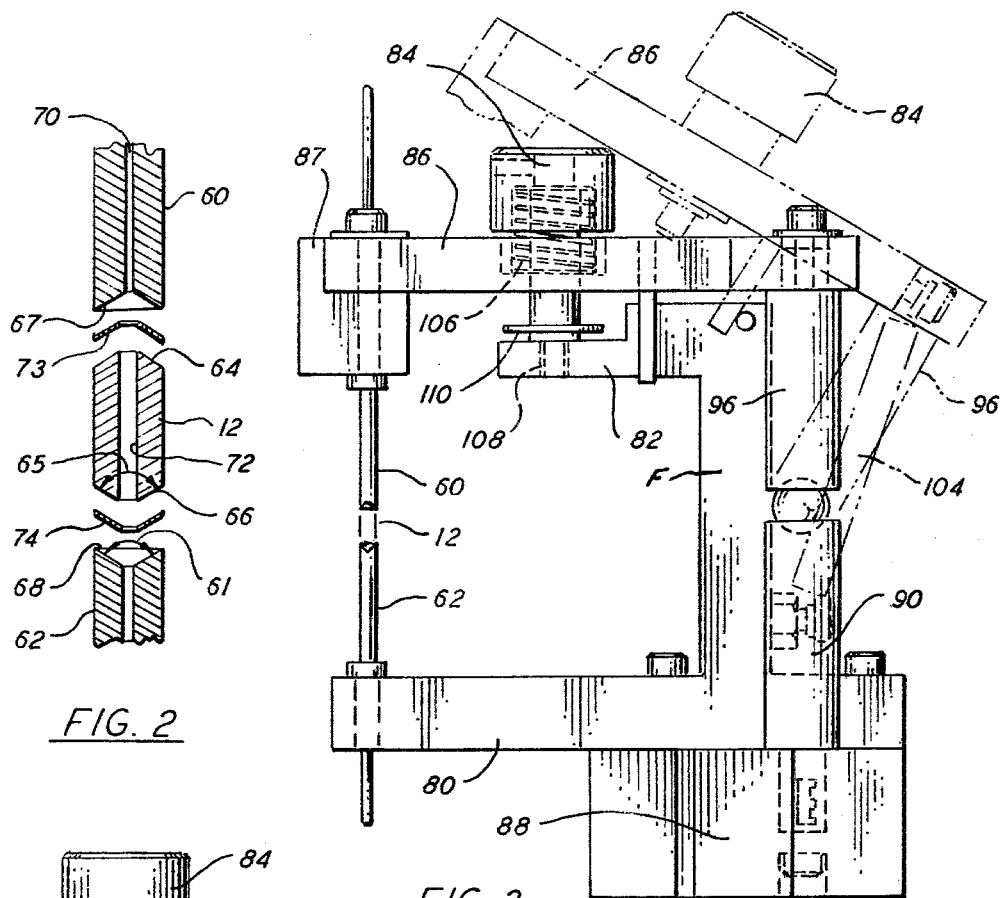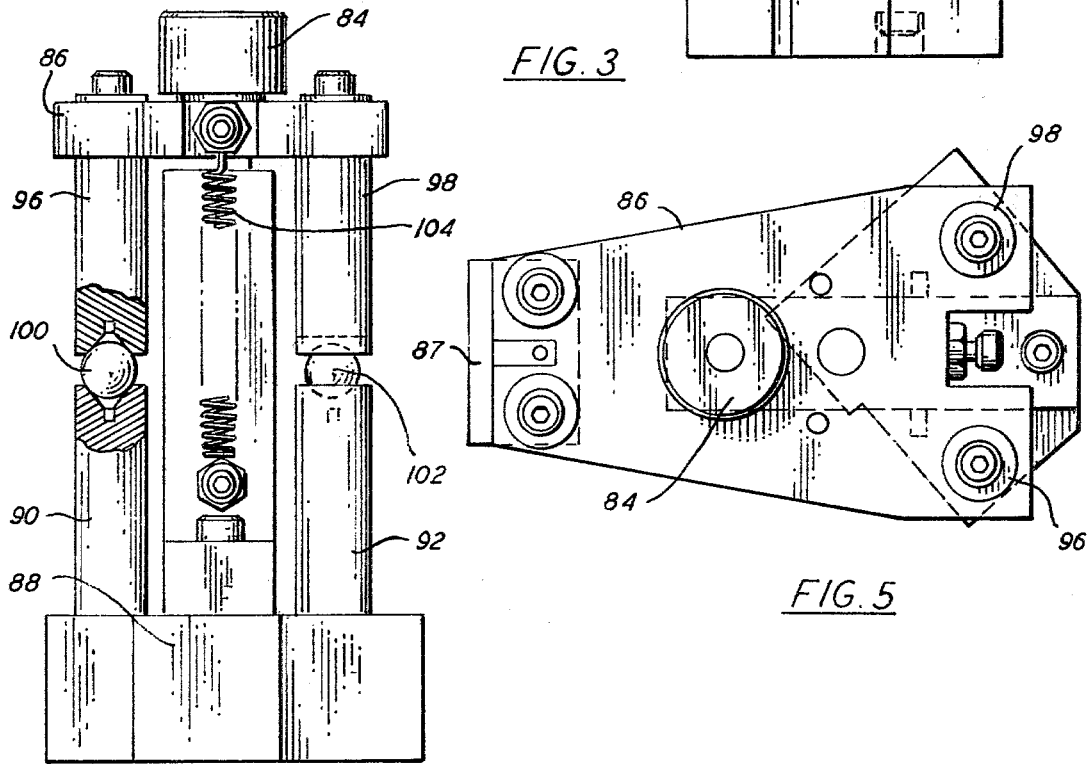

FLOW-THROUGH SAMPLE CELL AND COLLECTING AND ILLUMINATING OPTICS FOR LIQUID CHROMATOGRAPHY

BACKGROUND OF THE INVENTION

The present invention relates to apparatus for measuring radiation from a sample and particularly relates to radiation collecting and illuminating optics and a flow-through sample cell and mount therefor for a radiation detecting device, specifically a fluorescent liquid chromatography detector.

In radiation measuring apparatus of conventional construction, radiation is applied to a sample and the emission spectrum of the light from the sample is observed. Particularly, a first monochromator is utilized to disperse radiation from a light source and direct the radiation through an exit slit to the sample. An optical system is interposed to form the image of the monochromator exit slit in the sample. An additional optical system is utilized to direct the radiation from the sample to a second monochromator having entrance and exit slits, the latter optical system imaging the radiation from the sample at the entrance slit of the second monochromator. The second monochromator disperses radiation from the sample and directs it through an exit slit for detection by a detector and subsequent analysis.

In conventional instruments of the foregoing described type, the sample, which is subject to analysis, is disposed in a sample cell and is usually analyzed under static conditions. Attachments, however, have been provided for performing measurements on flowing samples. In both cases, images of the exit and entrance slits of the excitation and emission monochromators are focused in the sample cell.

In these conventional fluorescence spectrophotometers, lenses are normally utilized as the optics for directing the exit slit image of the first monochromator to the sample and the radiation from the sample to the entrance slit of the second monochromator for measurement. As is well known, lenses are subject to chromatic aberration. That is, their focus shifts when the lens transmits radiation of differing wavelengths. Thus, the excitation exit slit image and the radiation from the sample are focused at different points respectively in the sample cell and the emission entrance slit depending upon the wavelength of the radiation transmitted by the lenses. This is undesirable because resolution of the images at their design points is not maintained constant. Further, lenses diminish the energy throughput of the system due to reflection loss. This is significant because it is desirable to maximize the intensity of the light. Also, suitable lenses such as fused silica lenses are expensive to fabricate.

Further, it is desirable to utilize a small sample cell volume because it is more efficient and, in liquid chromatography applications, provides greater resolution. However, the use of small samples aggravates the aforementioned focusing problem inherent with lenses. In addition, lenses used in conjunction with very small sample cells, are increasingly expensive to fabricate because of their size and f number.

SUMMARY OF THE PRESENT INVENTION

It is a primary object of the present invention to provide a novel and improved apparatus for measuring radiation from a sample having increased energy throughput.

It is still another object of the present invention to provide a novel and improved apparatus for measuring radiation from a sample having optics specifically designed to provide higher energy density.

It is still another object of the present invention to provide a novel and improved apparatus for measuring radiation from a sample particularly useful in fluorescence liquid chromatography detection.

It is a further object of the present invention to provide a novel and improved apparatus for measuring radiation from a sample particularly for use with sample cells of small volume and which apparatus provides high resolution.

It is still a further object of the present invention to provide apparatus for measuring radiation from a sample cell, which may consist of a relatively inexpensive piece of quartz tubing, formed substantially without high quality optics.

It is a related object of the present invention to provide apparatus for measuring radiation from a sample having a novel and improved mount for the sample cell.

It is a related object of the present invention to provide apparatus for measuring radiation from a sample wherein interference from scattered light within the measuring apparatus is minimized or eliminated.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the present invention, as embodied and broadly described herein, apparatus for measuring radiation from a sample in accordance with the present invention comprises a source of radiation, a first monochromator for isolating a beam of monochromatic radiation from the radiation source. This first monochromator has an exit slit for passing the isolated excitation beam therethrough. Means are provided for focusing the isolated excitation beam, passing through the exit slit, at the sample, which include an ellipsoidal reflector for imaging the exit slit in the sample. A second monochromator serves to isolate a beam of monochromatic radiation from the sample. The second monochromator has an entrance slit, and means are provided for directing radiation from the sample to the entrance slit, including in one form thereof a second ellipsoidal reflector for imaging the radiation from the sample at the entrance slit. An isolated beam of monochromatic radiation from the sample is then directed to a radiation detector.

According to one aspect of the invention radiation blocking means or a baffle is mounted between the sample cell and the exit slit of the first monochromator and a second baffle is mounted between the sample cell and the entrance slit of the second monochromator to minimize or eliminate unwanted radiation.

In another aspect of the present invention, there is provided a holder for a sample cell comprising a base, an first mount for the sample cell carried by the base, an arm, a second mount for the sample cell carried by the arm. Means are provided for coupling the base and the arm for pivotal movement one relative to the other about an axis between a first position with the first mount and the second mount in spaced registration one with the other on opposite sides of the sample cell to hold the sample cell therebetween and a second position with the first mount and the second mount further spaced one from the other than in the first position to enable removal and disposition of a sample cell therebetween. The pivotal coupling means includes a pair of elements on the axis and cooperable surfaces respectively carried by the arm and the base and engaged with the elements to enable relative pivotal movement of the arm and the base about the axis. A pair of the surfaces and one of the elements have cooperating shapes to prevent relative movement of the arm and the base in a direction parallel to the axis, and another pair of the surfaces and another of the elements have cooperating shapes to permit relative movement of the surfaces of the other pair thereof in an axial direction, whereby repeatable accurate alignment of the mounts one with respect to the other in the first position thereof is obtained enabling accurate location of the sample cell therebetween.

The invention consists in the novel parts, construction, arrangements, conbinations, and improvements shown and described. The accompanying drawings which are incorporated in and constitute a part of the specification, illustrate one embodiment of the invention and, together with the description, serve to explain the principles of the invention.

BRIEF DESCRIPTION OF THE DRAWING FIGURES

FIG. 2 is a fragmentary enlarged cross sectional view with parts in exploded juxtaposition of the sample cell and mount therefor;

FIG. 3 is a side elevational view of the mounting assembly for the sample cell with the mount in an operative closed position;

FIG. 4 is an end elevational view of the mounting assembly with portions broken out and in cross section; and FIG. 5 is a top plan view thereof.

DETAILED DESCRIPTION OF A PREFERRED EMBODIMENT

Figure 1:
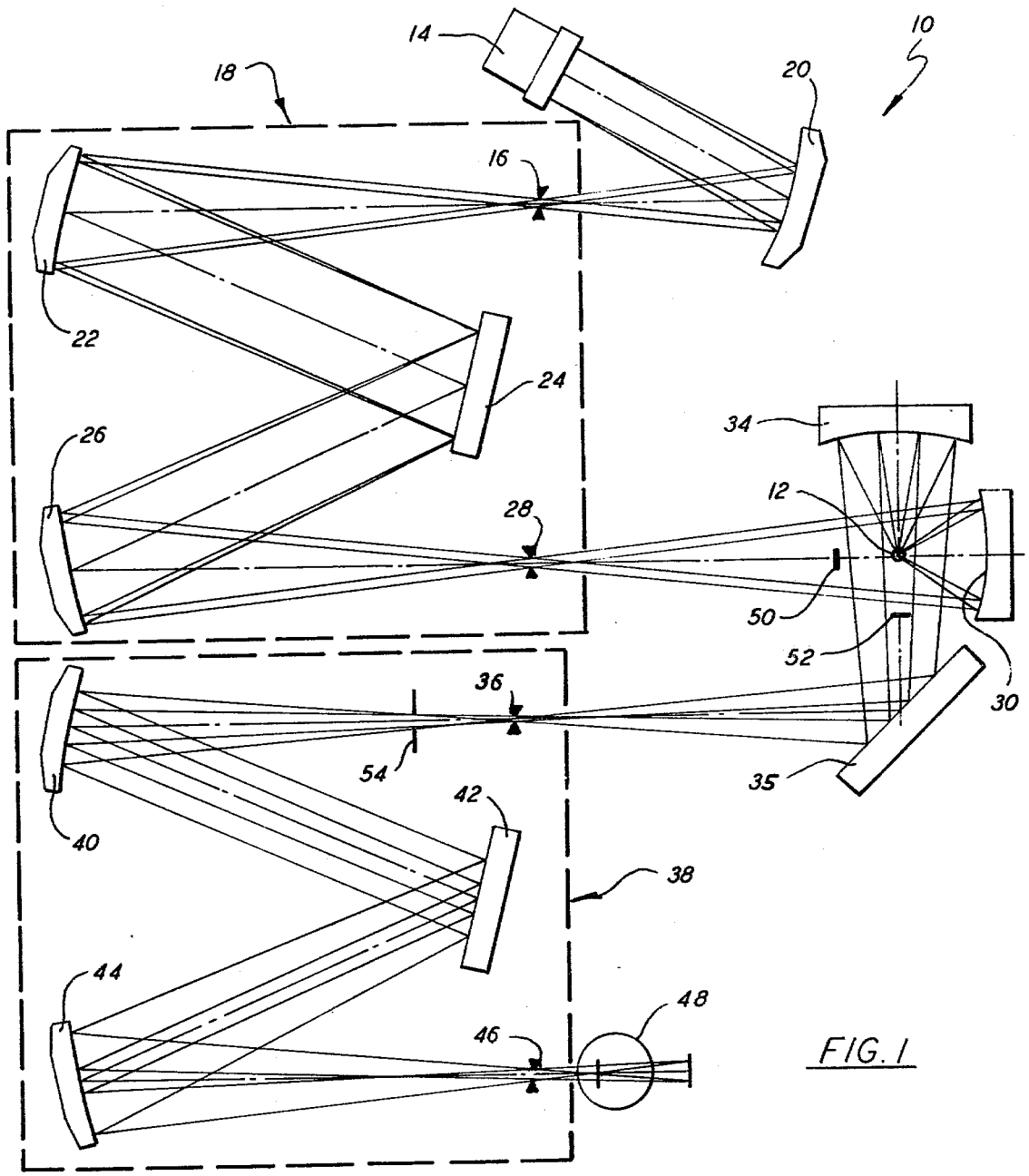
FIG. 1 is a schematic illustration of a radiation measuring device and specifically a fluorescence spectrophotometer constructed in accordance with the present invention and particularly illustrating the optical system.

Referring now to the drawings, particularly to FIG. 1, there is schematically illustrated, a fluorescence spectrophotometer, generally designated 10, for illuminating a sample in a sample cell 12 with radiation, e.g., intense monochromatic light, and collecting the emission from the sample for analysis. Particularly, radiation, e.g., light from a suitable source 14, such as a xenon arc lamp, is focused on the entrance slit 16 of a first monochromator, generally designated 18, by means of a focussing mirror 20. Monochromator 18 may in one desirable form be of the Czerney-Turner type and include a spherical mirror 22 for receiving the intense radiation from the light source 14 entering the monochromator through the entrance slit 16 and directing the radiation to a grating 24 for dispersion. Dispersed radiation is directed from grating 24 to a spherical mirror 26 which directs it through the exit slit 28, and exit slit 28 passes radiation having a preselected wavelength. Thus, the first monochromator 18, in combination with the radiation source 14, provides monochromatic radiation of a selected wavelength band through exit slit 28.

For focusing the monochromatic radiation exiting the first monochromator on and illuminating a sample in the sample cell 12, a first optical system is provided, which includes a first ellipsoidal reflector 30, for focusing the monochromatic radiation from exit slit 28 generally along the center line of the sample cell 12, i.e., substantially along the longitudinal axis of the sample cell 12. The exit slit 28 is disposed substantially at one focal point and the sample cell 12 is disposed substantially at the other focal point of the ellipsoidal reflector 30. It will be particularly appreciated that the first optical system is purely reflective and as a result of the absence of refractive optical elements the radiation from the exit slit 28 remains substantially in focus along the center line of the sample cell 12 in spite of changes in its wavelength.

Still referring to FIG. 1, the isolated monochromatic excitation beam focused on a flowing or stationary sample in sample cell 12 causes the sample to fluoresce and emit light in substantially all directions from the cell. A second optical system is provided to collect at least a portion of this emitted light from the sample and includes an ellipsoidal reflector 34 spaced from the cell 12. This collected radiation is directed to a flat mirror 35 and then to the entrance slit 36 of a second monochromator, generally indicaed at 38. The second optical system is similar to the first optical system. The sample cell 12 is disposed substantially at one focal point and the entrance slit 36 at the other focal point of the ellipsoidal reflector 34, thereby to focus the entrance slit 36 generally along the center line of the sample cell 12. The second optical system is also purely reflective and as a result the entrance slit 36 remains substantially in focus along the center line of the sample cell 12 in spite of changes in the wavelength of the radiation.

The second monochromator 38 includes a spherical mirror 40 for directing the emitted radiation from the sample received through entrance slit 36 to a grating 42 for wavelength dispersion. The emitted radiation is then directed from grating 42 to a spherical mirror 44. Mirror 44 directs this monochromatic emission beam through an exit slit 46, which passes radiation of the preselected wavelengths to a photodetector 48.

As in the conventional construction, the output signal from the photodetector is utilized in a conventional manner, as an indication of certain characteristics of the sample under investigation. In view of the fact that reflective optics are employed the system operates efficiently over a large range of wavelengths.

As seen in FIG. 1, to prevent or minimize scattering of radiation, a baffle 50 is disposed between sample cell 12 and the exit slit 28 of the first monochromator 18. Baffle 50 is located in the path of the monochromatic excitation beam in a position to block or prevent the direct impingement of the excitation beam from exit slit 28 on sample cell 12.

To prevent or minimize the scattering of radiation directly from the sample cell to the entrance slit 36 of the second monochromator 38, a second baffle 52 is disposed between sample cell 12 and the mirror 35 of the second optical system. That is, baffle 52 is located to block light scattered from the sample cell 12 along paths which would otherwise interfere with or mask the collected radiation directed by the ellipsoidal surface 34 for focusing at the entrance slit 36 of the second monochromator 38.

Still referring to FIG. 1, to further prevent scattered radiation from interfering with or masking the radiation from the sample collected by ellipsoidal surface 34 and directed thereby to the second monochromator entrance slit 38, a baffle or sample aperture 54 is disposed in the second monochromator 38 between the entrance slit 36 and the first mirror 40. This sample aperture 54 is so positioned as to be imaged adjacent the sample cell 12 on the side thereof between cell 12 and the ellipsoidal surface 34. By imaging the sample aperture 54 substantially tangent to the outer surface of sample cell 12 on the side thereof between cell 12 and surface 34, a limiting aperture for the radiation emitted from the sample and collected by ellipsoidal surface 34 is provided.

Turning now to the exploded view of FIG. 2, the sample cell 12 is mounted between tubular mounts or fittings 60 and 62 of a sample cell mounting assembly which will be described more fully hereinafter. The sample cell 12 is formed of a section of tubing, which is cut to length and has its ends conically ionically chamfered at 64 and 66, respectively. Quartz tubing may be employed as it is relatively inexpensive and commercially available and, in the present application, need not be optically exact. In one embodiment of the present invention, the sample cell 12 may comprise a quartz tube cut to a length of about 9/32 inch and have an outside diameter of about ⅛ inch. The flow passage through the tube may have an inside diameter of approximately 1/16 inch. The cone angle of chamfers 64 and 66, indicated at 65, is about 168°. The ends of the tubular mounts 60 and 62 are tapered as at 67 and 68 to substantially complement chamfers 64 and 66 respectively, but at a slightly larger included angle. For example, the tapers 67 and 68 have included angles indicated at 69 of about 174°. As indicated, the axial passage 70 through the tubular mount 60, as well as the passage through the tubular mount 62, are normally smaller in diameter than the diameter of the axial passage 72 through sample cell 12.

To seal the sample cell 12 between the tubular mounts 60 and 62, a pair of generally frustoconical tubular seals 73 and 74 are provided at the ends of the quartz tube, respectively. Seals 73 and 74 are tapered to coorespond to the mating chamfers and tapers of the sample cell and tubular mounts, respectively. The seals are of resilient material, such as polytetrafluoroethylene, for example, and because of their shape, they are self aligning with the tubes 60 and 62. When the assembly is in its compressed, operative position, each seal forms an inwardly extending circumferential bead, which ensures a fluid-tight, high pressure seal between the cell and the tubular mounts.

A best seen in FIGS. 3 to 5, the mounting assembly for the sample cell 12 includes a generally C-shaped frame F comprised of a base leg portion 80, which carries lower tubular mount or fitting 62 adjacent the distal end thereof, and an upper leg portion 82 which cooperates with a clamping screw 84 for purposes discussed thereinafter. Frame F is fixed to lower base 88 to which is also secured a pair of laterally spaced, tubular uprights 90 and 92, FIG. 4. An upper pivotal arm or bracket 86 overlies upper leg portion 82 and carries a mounting block 87 at its forward end for carrying fitting 60 in axial alignment with sample cell 12 and tubular fitting 62. Depending from upper arm 86 and at its opposite end from block 87 is a pair of tubular members 96 and 98.

To mount the upper arm 86 for pivotal movement, from its position as shown in solid lines to its position as shown in broken lines in FIG. 3, the ends of uprights 90 and 92 and tubular members 96 and 98 are respectively shaped to carry balls 100 and 102 therebetween. Particularly, the opposed ends of upright 90 and depending tubular member 96 have frustoconically shaped recesses which receive the ball 100 therebetween enabling universal pivotal action between upright 90 and member 96 except for the constraints imposed thereon as will be evident from the ensuring description. The end of upright 92 is similarly frustoconically shaped to receive the ball 102. The lower end of member 98, however, is provided with a generally cylindrical surface, having its long axis parallel to the upper arm 86. Thus, the ball 102 is disposed in the frustoconical recess of upright 92 and along the cylindrical surface of leg portion 98. Consequently, the upper arm 86 is pivotal about a transverse axis passing through the center of balls 100 and 102. The exact lateral position of arm 86 is maintained throughout its range of pivotal movement by ball 100 mating in the opposed frustoconical surface. Ball 102 and its mating cylindrical surface permit relative lateral movement of member 98 and upright 92. Thus, the balls cooperate with the surfaces engaged thereby to maintain repeatable accurate alignment of fittings 60 and 62 one with the other and with the sample cell 12 upon movement of the arm 86 toward the operative position, as indicated by the solid lines in FIG. 3, of the assembly with the sample cell sealed between the fittings.

A helical coil spring 104 is carried by the mounting assembly for maintaining the balls 100 and 102 in position. The ends of this spring are aligned, in the closed position of the mount as indicated by the solid lines in FIG. 3, substantially along a vertical axis coincident with a vertical plane containing the pivotal axes of balls 100 and 102 whereby constant pressure is maintained on balls 100 and 102 and arm 86 is maintained in its closed position. When the arm 86 is pivoted to its open position, as indicated by the broken lines in FIG. 3, the spring lies over center and thus maintains a bias force on arm 86 to hold it in the open position.

The clamping screw 84 is provided with an internal annular bore for receiving a spring 106, FIG. 3. This spring acts between the head of the screw 84 and the arm 86 to urge the arm downwardly with a peselected force. The bottom of the clamping screw 84 has a threaded portion which engages with mating threads in the upper leg portion 82, as indicated at 108. The screw is also provided with a shoulder portion 110. In operation, when the arm 86 is in its closed position, the operator rotates the screw 84 until the shoulder engages the upper leg portion 82. At this time the arm 86 is urged downwardly by only the force of the spring 106, thereby effecting a preselected clamping force on the clamping cell 12, indpendent of operator action.

Although a particular embodiment of the invention is disclosed for purposes of explanation, various modification thereof, after study of this specification, will be apparent to those skilled in the art to which the invention pertains.

What is claimed is:

1. Apparatus for measuring radiation from a sample comprising:
    a source of radiation,
    a first monochromator for isolating a beam of monochromatic radiation from said radiation source, said first monochromator having an exit slit for passing the isolated excitation beam therethrough, means for axially focusing the isolated excitation beam passing through said exit slit at the sample including a first ellipsoidal reflector with the exit slit disposed substantially at one optical focal point and the sample disposed substantially at the other optical focal point, a second monochromator for isolating a beam of monochromatic radiation from the sample and having an entrance slit, means for axially focusing radiation from the sample at the entrance slit of the second monochromator, and a radiation detector for receiving the isolated beam of monochromatic radiation from the sample.

2. Apparatus according to claim 1, wherein said means for focusing radiation from the sample at the entrance slit of the second monochromator comprises a second ellipsoidal reflector with the sample disposed substantially at one optical focal point and the entrance slit disposed substantially at the other optical focal point.

3. Apparatus according to claim 2, including an elongated sample cell for holding the sample, said sample cell being disposed so that the image of the longitudinal axis of the exit slit of the first monochromator is substantially coaxial with the longitudinal axis of the elongated sample cell, and the image of the longitudinal axis of the sample cell is substantially coaxial with the entrance slit of the second monochromator.

4. Apparatus according to claim 2 wherein said means for focusing radiation from the sample at the entrance slit of the second monochromator includes a folding mirror disposed between said second ellipsoidal reflector and said entrance slit.

5. Apparatus according to claim 2, further comprising baffle means disposed between the entrance slit of the second monochromator and the sample to block the direct radiation from the sample from impinging on the entrance slit.

6. Apparatus according to claim 1 or claim 5, further comprising baffle means disposed between the exit slit of the first monochromator and the sample to block the isolated excitation beam from impinging directly on the sample.

7. Apparatus according to claim 2 or claim 5 further comprising a sample aperture disposed adjacent the entrance slit within the second monochromator and positioned so as to be imaged adjacent the sample or the side thereof between the sample and the second ellipsoidal reflector to limit the radiation emitted by the sample.

8. Apparatus according to claim 3, further including a pair of axially aligned tubular mounts, one of said mounts being movable with respect to the other for clamping the sample cell therebetween, the ends of the sample cell being chamfered in the mating ends of the tubular mounts being tapered, the included angle of the chamfers being of the order of about 6° smaller than the included angles of the tapers, resilient frustoconically shaped tubular shaped seals with central apertures therein being interposed between the mating ends of the tubular mounts and the ends of the sample cell respectively to provide fluid tight high pressure seals respectively when the sample cell is clamped between the tubular mounts.

9. Apparatus for measuring radiation from a sample comprising:

a source of radiation, a first monochromator for isolating a beam of monochromatic radiation from said radiation source, said first monochromator having an exit slit for passing the isolation excitation beam therethrough, means for axially focusing the isolated excitation beam passing through said exit slit at the sample including a first ellipsoidal reflector with the exit slit disposed substantially at one optical focal point and the sample disposed substantially at the other optical focal point, a second monochromator for isolating a beam of monochromatic radiation from the sample and having an entrance slit, means for axially focusing radiation from the sample at the entrance slit of the second monochromator including a second ellipsoidal reflector with the sample disposed substantially at one optical focal point and the entrance slit disposed substantially at the other optical focal point, an elongated sample cell for holding the sample, said sample cell being disposed so that the image of the longitudinal axis of the exit slit of the first monochromator is substantially coaxial with the longitudinal axis of the elongated sample cell, and the image of the longitudinal axis of the sample cell being substantially coaxial with the entrance slit of the second monochromator, baffle means disposed between the exit slit of the first monochromator and the sample to block the isolated exitation beam from impinging directly on the sample, second baffle means disposed between the entrance slit of the second monochromator and the sample to block the direct radiation from the sample from impinging on the entrance slit, a sample aperture disposed adjacent the entrance slit within the second monochromator and positioned so as to be imaged adjacent the sample on the side thereof between the sample and the second ellipsoidal reflector to limit the radiation emitted by the sample, and a radiation detector for receiving the isolated beam of monochromatic radiation from the sample.

10. A holder for a sample cell comprising, a base, a first mount for the sample cell carried by said base, an arm, a second mount for the sample cell carried by said arm, means for coupling said base and said arm for pivotal movement one relative to the other about an axis between a first position with said first mount and said second mount in spaced relationship one with respect to the other on opposite sides of a sample cell to hold the sample cell therebetween and a second position with said first mount and said second mount further spaced one from the other than in said first position to enable removal and disposition of a sample cell therebetween, said pivotal coupling means including a pair of elements on said axis and cooperable surfaces respectively carried by said arm and said base and engaged with said elements to enable relative pivotal movement of said arm and said base about said axis, a pair of said surfaces and one of said elements having cooperating shapes to prevent relative movement of said arm and said base in a direction parallel to said axis and another pair of said surfaces and the other of said elements having cooperating shapes to permit relative movement of the surfaces of said other pair thereof in an axial direction whereby repeatable accurate alignment of said mounts one with respect to the other in said first position thereof is obtained enabling accurate location of the sample cell therebetween.

11. Apparatus according to claim 10 wherein one of said elements includes a spherical ball and the surfaces cooperable with said ball include opposing surfaces, and means for maintaining said surfaces and said elements engagable one with the other throughout the range of pivotal movement.

12. Apparatus according to claim 11 wherein the surfaces cooperable with said ball include conical surfaces.

13. Apparatus according to claim 11 wherein the other of said elements includes a spherical ball, one of the surfaces cooperating with one of the spherical balls including a tapered surface, the other of such surfaces cooperating with said one ball including a tapered surface symetrical about an axis parallel to said pivotal axis.

14. Apparatus according to claim 11 including a spring for biasing the arm and base toward one another to maintain the pivotal joint in assembled relation.

15. Apparatus according to claim 10 wherein said sample cell comprises a quartz tubing having a chamfered ends, each of the ends of said mounts being chamfered at an angle different than the angle of the chamfer at the corresponding end of the quartz tube to define an angle between each end of the tubing and its associated mounting in a direction outwardly of the axis of the tubing when the tubing and the mounts lie in assembled relation, and a frustoconically shaped seal with a central opening formed between each of the ends of said tubing and the corresponding mount, said seal being formed of a deformable material.

* * * * *

UNITED STATES PATENT AND TRADEMARK OFFICE
CERTIFICATE OF CORRECTION

PATENT NO. : 4,311,387
DATED : January 19, 1982
INVENTOR(S) : Charles F. deMey & Eugene F. Young It is certified that error appears in the above-identified patent and that said Letters Patent are hereby corrected as shown below:

Column 4, line 28, change "indicaed" to --indicated--.

Column 5, line 20, omit the word "ionically".

Column 5, line 44, change "coorespond" to --correspond--.

Column 5, line 54, change "A best" to --as best--.

Column 6, line 11, change "ensuring" to --ensuing--.

Column 6, line 47, change "peselected" to --preselected--.

Column 6, line 57, change "indpendent" to --independent--.

Column 8, line 13, change "focual" to --focal--.

UNITED STATES PATENT AND TRADEMARK OFFICE
CERTIFICATE OF CORRECTION

PATENT NO. : 4,311,387
DATED : January 19, 1982
INVENTOR(S) : Charles F. deMey & Eugene F. Young It is certified that error appears in the above-identified patent and that said Letters Patent are hereby corrected as shown below:

Column 6, line 60, change "modification" to --modifications--.

Column 8, line 33, change "exitation" to --excitation--.

Column 9, line 15, change "engagable" to --engageable--.

Column 10, line 4, change "symetrical" to --symmetrical--.

Column 10, line 9, omit the word "a" at the second occurrence thereof.

Signed and Sealed this

Eleventh Day of January 1983

[SEAL]

Attest:

Attesting Officer

GERALD J. MOSSINGHOFF

Commissioner of Patents and Trademarks